(12) United States Patent
Weller et al.

(10) Patent No.: US 6,869,588 B2
(45) Date of Patent: Mar. 22, 2005

(54) STIMULUS SENSITIVE GEL WITH RADIOISOTOPE AND METHODS OF MAKING

(75) Inventors: Richard E. Weller, Selah, WA (US); Michael A. Lind, Kent, WA (US); Darrell R. Fisher, Richland, WA (US); Anna Gutowska, Richland, WA (US); Allison A. Campbell, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/853,507

(22) Filed: May 9, 2001

(65) Prior Publication Data

US 2001/0024636 A1 Sep. 27, 2001

Related U.S. Application Data

(63) Continuation of application No. 09/058,712, filed on Apr. 10, 1998, now Pat. No. 6,296,831.

(51) Int. Cl.$^7$ .......................... A61K 51/00; A61M 36/14
(52) U.S. Cl. ...................... 424/1.29; 424/1.11; 424/1.37
(58) Field of Search ............................ 424/1.11, 1.29, 424/1.37, 1.65, 9.5, 9.51, 9.52, 9.1, 9.3, 9.4, 450; 128/662.02, 660.01, 653.1; 534/7, 10–16

(56) References Cited

U.S. PATENT DOCUMENTS

| | | | |
|---|---|---|---|
| 3,866,050 A | 2/1975 | Whitfield | 250/497 |
| 4,190,461 A | 2/1980 | Hedger | 134/1 |
| 4,510,924 A | 4/1985 | Gray | 128/1.2 |
| 4,754,745 A | 7/1988 | Horowitz | 128/1.2 |
| 4,763,462 A | 8/1988 | Johnson, Jr. et al. | 128/1.2 |
| H669 H | 9/1989 | Fairchild et al. | 600/3 |
| 5,213,580 A | 5/1993 | Slepian et al. | |
| 5,227,969 A | 7/1993 | Waggener et al. | 364/413.26 |
| 5,262,055 A | 11/1993 | Bae et al. | |
| 5,322,499 A | 6/1994 | Liprie | 600/8 |
| 5,424,288 A | 6/1995 | Order | 514/2 |
| 5,538,726 A | 7/1996 | Order | 424/178.1 |
| 5,561,698 A | 10/1996 | Mick et al. | 378/162 |
| 5,562,594 A | 10/1996 | Weeks | 600/3 |
| 5,575,815 A | 11/1996 | Slepian et al. | |
| 5,631,337 A | 5/1997 | Sassi et al. | 526/307.2 |
| 5,634,946 A | 6/1997 | Slepian | |
| 5,635,709 A | 6/1997 | Sliski et al. | 250/252.1 |
| 5,662,609 A | 9/1997 | Slepian | |
| 5,674,287 A | 10/1997 | Slepian et al. | |
| 5,702,717 A | 12/1997 | Cha et al. | 424/425 |
| 5,749,915 A | 5/1998 | Slepian | |
| 5,749,922 A | 5/1998 | Slepian et al. | |
| 5,762,903 A | 6/1998 | Park et al. | 424/1.29 |
| 5,820,879 A | 10/1998 | Fernandez et al. | 424/450 |
| 5,843,156 A | 12/1998 | Slepian et al. | |
| 5,942,209 A | 8/1999 | Leavitt et al. | 424/1.25 |
| 5,998,588 A | 12/1999 | Hoffman et al. | |
| 6,015,541 A | 1/2000 | Greff et al. | 424/1.25 |
| 6,290,729 B1 | 9/2001 | Slepian et al. | |
| 6,296,831 B1 * | 10/2001 | Weller et al. | 424/1.29 |
| 6,352,682 B2 | 3/2002 | Leavitt et al. | |
| 6,443,941 B1 | 9/2002 | Slepian et al. | |
| 6,486,213 B1 | 11/2002 | Chen et al. | |
| 2002/0168319 A1 | 11/2002 | Filler et al. | |

FOREIGN PATENT DOCUMENTS

| | | | |
|---|---|---|---|
| EP | 0730871 A1 | 9/1996 | 51/6 |
| WO | WO 95/24430 | 9/1995 | |
| WO | WO 9603112 | 2/1996 | |
| WO | WO 98/55147 | 12/1996 | |
| WO | WO 97/09068 | 3/1997 | 47/48 |
| WO | WO 97/33628 | 9/1998 | 51/12 |

OTHER PUBLICATIONS

Chen, G. et al., "Craft Copolymers that Exhibit Temperature–Induced Phase Transitions Over a Wide Range of pH," pp. 49–52 (1995).

Ning S. et al., "Intratumoral Radioimmunotherapy of a Human Colon Cancer Xengraft Using a Sustained–Release Gel," pp. 179–189 (1996).

Order, SE. et al., "Preliminary Experience of Infusional Brachytherapy Using Colloidal$^{32}$P," pp. 347–351 (1996).

"Copper Chelates as Probes of Biological Systems: Stable Copper Complexes with a Macrocyclic Bifunctional Chelating Agent", by MK Moi et al., p. 249–253. 1985.

"Environmentally Sensitive Polymers and Hydrogels", by AS Hoffman, p. 42–46. 1991.

"Gelation of Globular Proteins: Effect of pH and Ionic Strength on the Critical Concentration for Gel Formation. A Simple model and its application to β–Lactoglobulin Heat–Induced Gelation.", p. 287–291. 1992.

"Hawley's Condensed Chemical Dictionary",by RJ Lewis, Sr., p. 28, 124–125, 256, 785. 1993.

(List continued on next page.)

Primary Examiner—Dameron L. Jones
(74) Attorney, Agent, or Firm—Klarquist Sparkman, LLP (57) ABSTRACT

The present invention is a thermally reversible stimulus-sensitive gel or gelling copolymer radioisotope carrier that is a linear random copolymer of an [meth-]acrylamide derivative and a hydrophilic comonomer, wherein the linear random copolymer is in the form of a plurality of linear chains having a plurality of molecular weights greater than or equal to a minimum gelling molecular weight cutoff. Addition of a biodegradable backbone and/or a therapeutic agent imparts further utility. The method of the present invention for making a thermally reversible stimulus-sensitive gelling copolymer radionuclcide carrier has the steps of: (a) mixing a stimulus-sensitive reversible gelling copolymer with an aqueous solvent as a stimulus-sensitive reversible gelling solution; and (b) mixing a radioisotope with said stimulus-sensitive reversible gelling solution as said radioisotope carrier. The gel is enhanced by either combining it with a biodegradable backbone and/or a therapeutic agent in a gelling solution made by mixing the copolymer with an aqueous solvent.

25 Claims, 2 Drawing Sheets

OTHER PUBLICATIONS

"Hydrogels in Medicine and Pharmacy", vol. II Polymers, by NA Peppas, p. 115–160, 1987.

"Intelligent Gels", by Y Osada et al., p. 82–87. 1993.

"Intratumoral Radiommunotherapy of a Human Colon Cancer Xenograft Using a Sustained–Release Gel", by Ning et al., p. 179–189. 1996.

"Lower Critical Solution Temperatures of Aqueous Copolymers of N–Isopropylacrylamide and Other N–Substituted Acrylamides", by JH Priest et al., p. 255–264. 1987.

"Phase Transitions in Cross–Linked Gels of Natural Polymers", by T Amiya et al., p. 1162–1164. 1987.

"Polymer Communications", by Q Yan et al., p. 887–889. 1995.

"Synthesis Characterization, and $1/T_1$ NMRD Profiles of Gadolinium (III) Complexes of Monoamide Derivatives of DOTA–Like Ligands." By. S Aime et al., p. 2422–2428. 1991.

"Synthesis and Characterization of the Gadolinium (3+) Complex of DOTA–Propylamide: A Model DOTA–Protein Conjugate." By. AD Sherry et al., p. 620–622. 1989.

"Temperature Dependence of Swelling of Crosslinked Poly(N, N'–Alkyl Substituted Acrylamides) in Water." by, YH Bae et al., p. 923–936. 1990.

"Thermosensitive Polymers for Drug Delivery", by A Gutowska et al., p. 115–116. 1996.

Vernon, Brent et al., "Thermally Reversible Polymer Gels for Biohybrid Artificial Pancreas," Macromol. Symp., vol. 109, pp. 155–167 (1996).

* cited by examiner

Fig. 3b ized as an int
STIMULUS SENSITIVE GEL WITH RADIOISOTOPE AND METHODS OF MAKING This application is a Continuation Application of application Ser. No. 09/058,712 filed Apr. 10, 1998, now U.S. Pat. No. 6,296,831.

This invention was made with Government support under Contract DE-AC06 76RLO 1830 awarded by the U.S. Department of Energy. The Government has certain rights in the invention.

FIELD OF THE INVENTION

The present invention relates generally to a stimulus sensitive gel containing a radioisotope or radionuclide and method of making. As used herein, the term "stimulus sensitive gel" is a polymer solution that gels upon a change in stimulus. A stimulus includes but is not limited to temperature, pH, ionic strength, solvent composition, sheer stress or a combination of these factors. The preferred gel is generally a reversible gel, more specifically; the gel is a random copolymer of an [meth-]acrylamide derivative with a hydrophilic comonomer. As used herein, the term [meth]-acrylamide denotes methacrylamide, acrylamide, or combinations thereof. As used herein, the terms "radioisotope" and "radionuclide" are synonymous.

BACKGROUND OF THE INVENTION

Radiolabelling as a method of diagnosis or treatment has been in use for many years. The continuing challenge has been to maximize concentration of the radioisotope in the area or region of interest, diseased tissue or tumor, while minimizing the concentration of the radioisotope in other areas and thereby minimizing damage to healthy tissues.

The paper by S. Ning, K. Trisler, D. M. Brown, N. Y. Yu, S. Kanekal, M. J. Lundsten, S. J. Knox: "Intratumoral radioimmunotherapy of a human colon cancer xenograft using a sustained-release gel", Radiotherapy and Oncology, 39, 179–189, 1996 discusses an intratumoral injectable gel drug delivery system for local administration of radio-immunotherapy. The injectable gel was a collagen-based drug delivery system designed for intratumoral administration. The study demonstrated that intratumoral delivery of radiolabeled antibodies using the collagen gel system markedly increased the retention of radioisotope in the tumors, enhanced the antitumor efficacy, and reduced the systemic toxicity compared to systemic administration of the radiolabeled antibody. Ning et al. teach the use of injectible collagen gels that are not stimuli-sensitive. Moreover, these collagen gels neither fully perfuse tumor tissue nor do they hold the radioisotope within the collagen gel matrix. Thus, the radioisotope is attached to an antibody for perfusing and binding to the tumor tissue. Lack of perfusion of the collagen gel and limited range of radioisotope decay products require that the radioisotope leave the collagen gel matrix to achieve close proximity with tumor tissue to achieve the therapeutic effect.

In the paper PRELIMINARY EXPERIENCE OF INFUSIONAL BRACHYTHERAPY USING COLLOIDAL $^{32}$P, S E Order, J A Siegel, R Principato, L S Zieger, E Johnson, P Lang, R Lustig C Kroprowski, P E Wallner, Annals Academy of Medicine, May 1996, Vol. 25, No. 3, an infusion by a needle into a tumor was done without the need for an arterial catheter and eliminating the need for hospitalization. This paper reports using dexamethasone (Decadron) to overcome intratumoral resistance followed by macroaggregated albumin then colloidal chromic phosphate $^{32}$P followed by more macroaggregated albumin injected into the tumor. Sufficient radiation emitted by the radioisotope leads to tumor cell killing and remission of solid cancers. However, disadvantages of this method include the serial injections and leakage of $^{32}$P from the tumor.

There is need in the art for a method of introducing a radioisotope into a localized area with a single or multiple injection(s) as well as a need for a local delivery system with little or reduced leakage of the radioisotope.

Stimulus-sensitive reversible hydrogels are herein defined as copolymer-solvent systems that undergo a transition between a solution and a gel state in response to the external stimuli such as temperature, pH, ionic strength, solvent composition, sheer stress or a combination of these factors. A reversible stimuli-sensitive gel is one in which the transition is reversed upon reversal of the stimulus. A well known example of a reversible hydrogel is an aqueous solution of gelatin that is in a solution state at high temperatures (e.g. 80° C.) and forms a gel at lower temperatures (e.g., 20° C.). Other examples of reversible gels involve aqueous solutions of agarose and kappa-carrageenan that gel in response to the temperature change, and aqueous solutions of alginate that gel in response to the increased concentration of calcium ions. Reversible hydrogel systems are used in food and pharmaceutical industries as thickeners and suspending agents.

Some specific reversible gelling copolymers were also investigated as drug delivery systems and tissue engineering polymer matrices. High viscosity aqueous solutions containing 20 (or more) wt % of block copolymers of polyethylene oxide and polypropylene oxide, e.g. Poloxamer 407 and Pluronic F68 (Poloxamer 188) exhibit reverse thermal gelation. Solutions of Poloxamer 407 have been investigated for intraocular administration. Solutions containing 25 and 30 wt % of Poloxamer 407 have been prepared and the force needed to inject them through a 25 GA needle was investigated. It was concluded that a liquid-gel transition occurred inside the needle, due to the heat transfer between the needle walls and the surroundings. [J. Juhasz, A. Cabana, A. Ait-Kadi, EVALUATION OF THE INJECTION FORCE OF POLOXAMER 407 GELS FOR INTRAOCULAR ADMINISTRATION, Pharm.Res., 13, No.9, 1996, Symposium Supplement, S-276].

In another example, 25 wt % aqueous solution of Pluronic F68 was mixed with articular chondrocyte cells suspension at 4° C. and injected subcutaneously in nude and immunocompetent rabbit. In both cases, the cells entrapped in the copolymer formed tissue with histological appearance of hyaline cartilage. It was concluded that thermally reversible Pluronic F68 gel can serve as an effective injectable matrix for tissue engineering. [C. A. Vacanti, et al., Proceedings of Tissue Engineering Society, Orlando, Fla., 1996].

An example of a pH-reversible hydrogel, investigated as an in situ gelling system for ophthalmic use is the aqueous solution of, a poly(acrylic acid)polymer, which undergoes a pH-mediated phase transition at concentrations above 0.1 wt %. The solution also contains hydroxypropyl methylcellulose, a viscosity enhancing agent. [Pharm.Res., 13, No.9, 1996, Symposium Supplement].

A new vehicle for topical and mucosal delivery, based on reversible gelation, was developed as an interpenetrating polymer network (IPN) of poly(acrylic acid) and a block copolymer of poly(ethylene oxide)/poly(propylene oxide). When heated from ambient to body temperature the network exhibited a significant viscosity increase from a viscous liquid to a gel-like consistency. It was concluded that at higher temperature, reduced release rates of active ingredients from the network were observed due to the increased viscosity of the IPN. [E. S. Ron, et al., A NEW VEHICLE FOR TOPICAL AND MUCOSAL DRUG DELIVERY, Pharm.Res., 13, No.9, 1996, Symposium Supplement, S-299].

All gels containing the copolymers of poly(ethylene oxide)/poly(propylene oxide), i.e., Poloxamer 407, Pluronic F68 (Poloxamer 188), an IPN of poly(acrylic acid) and a block copolymer of poly(ethylene oxide)/poly(propylene oxide), and combinations thereof exhibit a limited, concentration dependent, stability of the gel state. The gels formed from these copolymers become liquids upon dilution (as for example due to the dilution with body fluids after peritoneal injection). Additionally, all the above examples of reversible hydrogels exhibit high initial viscosity in a liquid state, i.e., before the gelling transition.

Accordingly there is a need for a reversible gel that only reverses when a specific stimulus is reversed and does not reverse upon introduction of a different stimulus (e.g. dilution). Moreover, there is a need for a reversible gel that has a lower initial viscosity.

The U.S. Pat. No. 5,262,055 to Bae et al. discusses an artificial pancreas utilizing reversible gels based on NiPAAM and its copolymers. These polymers and copolymers do not reverse upon dilution and they have a lower initial viscosity. However, the NiPAAM homopolymer described in Example 1 of Bae et al. forms a dense gel with minimal water content (i.e. exhibits substantial syneresis).

Accordingly, there remains a need for a thermally reversible gel without substantial syneresis.

Polymers exhibiting phase transitions in water have many potential uses for drug delivery as stated in GRAFT COPOLYMERS THAT EXHIBIT TEMPERATURE-INDUCED PHASE TRANSITIONS OVER A WIDE RANGE OF pH, G. Chen, A S Hoffman, Nature, Vol 373, 5 Jan. 1995 (pp49–52). In this paper, the authors further describe a temperature sensitive polymer that phase separates with a change in temperature or pH. Chen and Hoffman use graft copolymers having side chains of a temperature sensitive homopolymer, the oligo-N-isopropylacrylamide, grafted onto a pH sensitive backbone homopolymer of acrylic acid. The authors describe the phase separation of the graft copolymer investigated by a cloud point determination in dilute solutions. However, a dilute solution cannot produce a reversible gelation of these graft copolymers. Chen and Hoffman also mention random copolymers of N-isopropylacrylamide and acrylic acid as exhibiting a phase separation, however, there is no description of the intention to study the possibility of reversible gelation in more concentrated solutions of these random copolymers.

Thus, there is a need for a stimulus sensitive gel with radioisotope that is useful in infusional brachytherapy.

SUMMARY OF THE INVENTION

The present invention is a radioisotope carrier made by combining a stimulus sensitive gel with either an aqueous insoluble or confined radioisotope. A preferred stimulus sensitive gel is a thermally reversible gel or thermally reversible gelling copolymer that is preferably a random copolymer of an [meth-]acrylamide derivative and a hydrophilic comonomer, wherein the random copolymer is in the form of a plurality of linear chains having a plurality of molecular weights greater than or equal to a minimum gelling molecular weight cutoff. The thermally reversible gelling copolymer is enhanced by either combining it with a therapeutic agent in an aqueous solution containing the thermally reversible gelling copolymer, and/or by grafting the thermally reversible gelling copolymer to a biodegradable backbone. The stimulus sensitive gel may also be selected from biodegradable polymers, for example polysaccharides, polypeptides and combinations thereof; cellulose derivatives including but not limited to hydroxypropylmethyl cellulose; other polymers such as agar, gelatin, chitosan, alginate in combination with a slow gelling agent for example calcium sulfate and combinations thereof.

The method of the present invention for making a radioisotope carrier has the steps of:

(a) mixing a stimulus-sensitive gelling polymer with an aqueous solvent as a stimulus-sensitive gelling solution; and (b) mixing an aqueous non-soluble or confined radioisotope with the stimulus-sensitive reversible gelling solution as the radioisotope carrier.

Aqueous non-soluble radioisotope is a radioisotope in a colloidal or precipitate form, for example radioisotope insoluble salt, e.g. yttrium phosphate, radium sulfate, and combinations thereof. Confined radioisotope is radioisotope in a chelator, glass particle, polymer particle or other binding compound.

A preferred stimulus-sensitive gelling polymer is a thermally reversible gelling copolymer, preferably made according to the steps of:

(a) mixing an [meth-]acrylamide derivative with a hydrophilic comonomer in a solvent with an initiator forming a reaction mixture;

(b) polymerizing the reaction mixture and forming a first random copolymer having a plurality of linear chains having a plurality of molecular weights; and (c) purifying the polymerized first random copolymer and obtaining a second random copolymer having a plurality of molecular weights greater than or equal to a minimum gelling molecular weight cutoff. The method has the further steps of combining the thermally reversible gelling copolymer with a radioisotope in an aqueous solution containing the thermally reversible gelling copolymer.

It will be apparent to one of skill in the art of radiotherapy that an image enhancer or contrast agent may be added to the stimulus sensitive gelling polymer, for example as used in nuclear medicine imaging, ultrasonic imaging, and magnetic resonance imaging (MRI).

Advantages of the present invention include (1) the stimuli-sensitive gel of the present invention exhibits a thermodynamic stability, and when geled, will not reverse to the liquid state upon dilution but may reverse to the liquid state only in response to a stimulus change. Moreover, the stimuli-sensitive gel of the present invention in a solution state has lower initial viscosity more suitable for tissue perfusion.

It is an object of the present invention to provide a radioisotope carrier.

It is a further object of the present invention to provide a method of making a radioisotope carrier.

It is a further object of the present invention to provide a biodegradable stimuli-sensitive polymer useful for a radioisotope carrier.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

The present invention is a radioisotope carrier having a stimulus-sensitive gelling polymer mixed with aqueous solvent and with a radioisotope that is either aqueous non-soluble or confined as the radioisotope carrier.

The radioisotope is preferably an alpha and/or beta emitter with a short half life. More specifically, the radioisotope is selected from the group of yttrium-90, indium-111, radium-223, actinium-225, bismuth-212, bismuth-213, scandium-47, astatine-211, rhenium-186, rhenium-188, iodine-131, iodine-124, lutetium-177, holinium-166, samarium-153, copper-64, copper-67, phosphorus-32 and combinations thereof.

In a preferred embodiment, the radioisotope carrier further has a radioisotope confine. The purpose of the radioactive confine is to minimize or prevent migration of the radioisotope to healthy tissue areas. The radioisotope confine may be for example chelators or complexing agents, capsules and combinations thereof. Preferred isotope/chelator combinations are yttrium-90 or indium-111 with 1,4,7,10-tetraazacyclododecane-N,N',N'',N'''-tetraacetic acid (DOTA), derivatives of DOTA; radium-223 with tetra-t-butyl-calix[4]arene-crown-6-dicarboxylic acid (TBBCDA), derivatives of TBBCDA; actinium-225 with 5,11,17,23-tetra-t-butyl-25,26,27,28-tetrakis (carboxymethoxy)-calix[4]arene (TBTC), derivatives of TBTC; and bismuth-212, bismuth-213 with 5,11,17,23,29, 35-hexa-t-butyl-37,38,39,40,41,42-hexakis (carboxymethoxy)-calix[6]arene (HBHC), derivatives of HBHC, diethylenetriamine-pentaacetic acid (DTPA), or ethylenediaminetetraacetic acid (EDTA), derivatives of DTPA, and combinations thereof.

The radioisotope confine may be glass beads and/or polymer beads.

The stimulus-sensitive gelling polymer may be selected from biodegradable polymers, for example polysaccharides, polypeptides and combinations thereof; cellulose derivatives including but not limited to hydroxypropylmethyl cellulose; other polymers such as agar, gelatin, collagen, chitosan, alginate with a slow gelling agent for example calcium phosphate, gelling copolymer and combinations thereof. A preferred polymer is a polymer that is useful as a gel that forms without substantial syneresis when the stimulus-sensitive polymer is in an aqueous solution. Syneresis is defined as water expelled from a polymer matrix upon gelation. Substantial syneresis is more than about 10 wt % water expelled from the polymer matrix. According to the present invention, it is preferred that the syneresis be less than about 10 wt %, more preferably less than about 5 wt % and most preferably less than about 2 wt %. Substantially no syneresis is syneresis of less than about 2 wt %, preferably 0 wt %.

Figure 1:
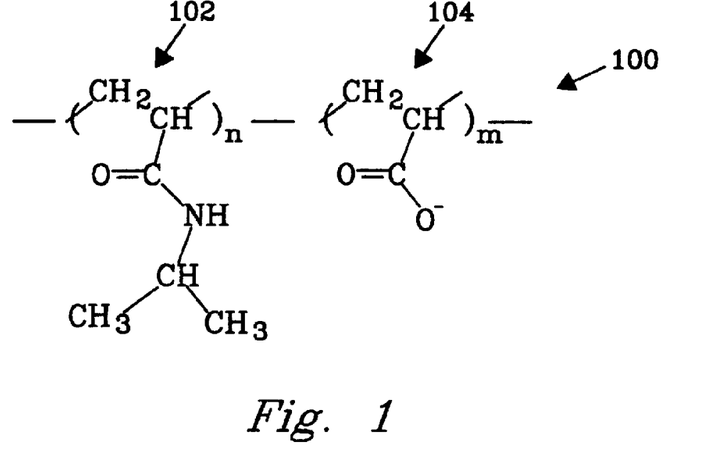
FIG. 1 is a depiction of a random copolymer of poly(N-isopropylacrylamide-co-acrylic acid) (NiPAAm/AAc), where n and m denote sequences of NiPAAm and AAc (respectively) that are of random length and are randomly distributed along the copolymer chain.

The thermally reversible copolymer is a linear random copolymer of an [meth-]acrylamide derivative and a hydrophilic comonomer wherein the linear random copolymer is in the form of a plurality of linear chains having a plurality of molecular weights greater than or equal to a minimum gelling molecular weight cutoff. According to the present invention, the minimum gelling molecular weight cutoff is at least several thousand and is preferably about 12,000. The presence of a substantial amount of copolymer or polymer chains having molecular weights less than the minimum gelling molecular weight cutoff results in a milky solution that does not gel. Further, the amount of hydrophilic comonomer in the linear random copolymer is preferably less than about 10 mole %, more preferably less than about 6 mole % and most preferably about 2–5 mole %. The structure of linear chains is not cross linked. Moreover, the linear random copolymer structure is one in which a linear chain 100 is shared by randomly alternating portions of the [meth-]acrylamide derivative 102 and the hydrophilic comonomer 104 as depicted in FIG. 1.

The [meth-]acrylamide derivative is an N,N'-alkyl substituted [meth-]acrylamide including but not limited to N-isopropyl[meth-]acrylamide, N,N'-diethyl[meth-]acrylamide, N-[meth-]acryloylpyrrolidine, N-ethyl[meth-]acrylamide, and combinations thereof.

The hydrophilic comonomer is any hydrophilic comonomer that co-polymerizes with the [meth-]acrylamide derivative.

Preferred hydrophilic comonomers are hydrophilic [meth-]acryl-compounds including but not limited to carboxylic acids, [meth-]acrylamide, hydrophilic [meth-]acrylamide derivatives, hydrophilic [meth-]acrylic acid esters. The carboxylic acid may be, for example, acrylic acid, methacrylic acid and combinations thereof. The hydrophilic acrylamide derivatives include but are not limited to N,N-diethyl[meth-]acrylamide, 2-[N,N-dimethylamino] ethyl[meth-]acrylamide, 2-[N,N-diethylamino]ethyl[meth-] acrylamide, or combinations thereof. The hydrophilic [meth-]acrylic esters include but are not limited to 2-[N,N-diethylamino]ethyl[meth-]acrylate, 2-[N,N-dimethylamino] ethyl[meth-]acrylate, and combinations thereof.

According to the present invention, the stimulus-sensitive polymer may be mixed with an aqueous solvent to form a stimulus-sensitive gelling solution, or reversible gelling solution. The aqueous solvent includes but is not limited to water and aqueous salt solutions. The salt solution is preferably a phosphate buffered saline solution for medical use.

The method of making the thermally reversible polymer according to the present invention has the steps of:

(a) mixing an [meth-]acrylamide derivative with a hydrophilic comonomer in a reaction solvent with an initiator forming a reaction mixture;

(b) polymerizing the reaction mixture and forming a first linear random copolymer having a plurality of linear chains having a plurality of molecular weights; and (c) isolating and purifying the polymerized first linear random copolymer and obtaining a second linear random copolymer having a plurality of molecular weights greater than or equal to a minimum gelling molecular weight cutoff.

The alternatives for the [meth-]acrylamide derivative and the hydrophilic comonomer have been set forth above and are not repeated here.

The reaction solvent may be aqueous or non-aqueous. The preferred aqueous solvent is simply water. Alternatively, the aqueous solvent is a salt solution. The non-aqueous solvent may be a hydrocarbon including but not limited to oxygenated hydrocarbon solvent, for example dioxane, chlorinated hydrocarbon solvent, for example chloroform, an aromatic hydrocarbon, for example benzene. Precipitation of the polymer occurs during polymerization in benzene. Dioxane is the preferred solvent because there is no precipitation during copolymerization thereby imparting greater uniformity of composition of the random copolymer (NiPAAM/AAc).

The amount of aqueous solvent with respect to [meth-]acrylamide derivative is preferably about 80 wt %, but may range from about 30 wt % to about 98 wt %. The amount of non-aqueous solvent with respect to the [meth-]acrylamide derivative is preferably about 80 wt % but may range from about 30 wt % to about 98 wt %.

The initiator may be any free radical initiator compatible with the [meth-]acrylamide derivative. The preferred initiator is 2,2'-azobis-isobutyrolnitrile (AIBN). The amount of the initiator with respect to the reaction mixture of solvent and polymer is preferably about 0.1 wt % but may range from about 0.01 wt % to about 2 wt %.

A reversible gelling solution is made by mixing the thermally reversible polymer with an aqueous solution. The amount of aqueous solution with respect to polymer is from about 70 wt % to about 99 wt %, preferably about 98 wt % for NiPAAm/AAc to achieve a nonresorbable reversible gel with substantially no syneresis. The aqueous solution is preferably a salt solution.

In addition to the nonresorbable reversible gel composed of a linear random copolymer of N-isopropyl[meth-]acrylamide and [meth-]acrylic acid described in this invention, a biodegradable (resorbable) copolymer exhibiting similar gelation properties is obtained by grafting of the oligo [meth-]acrylamide derivative side chains on a biodegradable homopolymer backbone of, e.g., poly(amino acid). Preferred oligo [meth-]acrylamide derivative side chains include N,N-alkyl substituted [meth-]acrylamide derivatives, linear random copolymer of [meth-]acrylamide derivative and hydrophylic comonomer, and combinations thereof. Techniques of grafting of oligo-N-isopropyl[meth]acrylamide side chains on a nonbiodegradable pH-sensitive homopolymer backbone are described (Chen and Hoffman). The technique(s) of Chen and Hoffman were used herein to graft the oligo-N-isopropyl[meth-]acrylamide side chains on an alternative biodegradable homopolymer backbone such as poly(amino acid). The first step of the synthesis is either the free-radical homopolymerization or the random copolymerization of the oligo-N-isopropyl[meth-]acrylamide side chains by free radical homopolymerization using an amino-terminated chain transfer agent, for example 2-aminoethanethiol hydrochloride. The next step is the coupling of the amino-terminated macromer to the carboxyl moieties of the biodegradable backbone using the activation reagent, e.g., dicyclohexyl carbodiimide. Other biodegradable backbones such as poly(phosphazenes) and poly (caprolactone) may also be grafted with the oligo-N-isopropyl[meth-]acrylamide side chains using similar synthetic techniques. The reaction solvent is non-aqueous, preferably a hydrocarbon, for example chloroform, dichloromethane, N,N'-dimethylformamide or combinations thereof.

The resorbable and/or non-resorbable stimulus-sensitive gel(s) of the present invention is/are useful as a radioisotope carrier for infusional brachytherapy.

One or more contrast or imaging agents may be added to the stimulus sensitive gelling polymer. For nuclear medicine imaging, any gamma-emitting radioisotope may be added to the gel polymer as an imaging agent or contrast agent. The common types of gamma source imaging systems are gamma-cameras (Anger cameras), single-photon emission computed tomography (SPECT), and positron-emission tomography (PET). Preferred imaging agents for gamma cameras would be technetium-99m (and any of the standard chemical forms of Tc-99m, such as pertechnetate). The preferred chemical form of Tc-99m may be an insoluble material, such as Tc-99m-sulfur colloid (a common liver scanning agent). Other gamma emitters include but are not limited to indium-111, rhenium-186, rhenium-188, thallium-201, gallium-67, yttrium-91, and iodine-131, and combinations thereof. Positron-emission tomography systems use positron-emitting radioisotopes and detect the twin 0.511 keV photons that accompany radioactive decay. Examples of radioisotopes that could be added for positron-emission tomography include fluorine-18, copper-64, arsenic-74, and zirconium-89, ioding-124, and yttrium-86. A typical amount of photon-emitter added is one that will provide approximately 500,000 counts per two-minute imaging time (0.3 to 10 millicuries).

For ultrasonic imaging, any ultrasound contrast-enhancement agent could be added to render the gel polymer more imageable using ultrasonic detection. Examples include commercially available echocontrast products such as Albunex® (registered trade mark, Molecular Biosystems) and Optison™ (trade mark of Molecular Biosystems), which are manufactured for and distributed by Mallinckrodt Medical, St. Louis, Mo. Albunex® is an ultrasound contrast agent prepared by sonicating 5% human serum albumin to produce stable, air-filled, albumin-coated microspheres. It is an effective ultrasound contrast agent for use during echocardiography and other ultrasound radiological procedures. Optison™ is an ultrasound contrast agent containing human serum albumin with octofluoropropane. Each milliliter of echocontrast agent contains about 700 million microspheres. The amount of contrast agent added could be approximately 1 to 5 percent by weight of the gel polymer.

For magnetic resonance imaging (MRI), any paramagnetic material used for contrast-enhancement may be used. An example includes a relaxation agent gadolinium-chelate (gadolinium-DTPA or gadolinium-EDTA). The stable (nonradioactive) form of gadolinium is preferred. The amount of gadolinium contrast agent added would be a few parts per thousand by weight (millimolar concentrations).

EXAMPLE 1

An experiment was conducted to demonstrate synthesis and thermoreversible gel formation of poly(N-isopropylacrylamide-co-acrylic acid)(NiPAAm/AAc). The linear high molecular weight NiPAAm/AAc copolymers containing different amounts of AAc were synthesized by a free radical copolymerization.

The [meth-]acrylamide derivative was N-isopropylacrylamide (NiPAAm) (Fisher, Co.) that was recrystallized from hexane before use. The initiator 2,2'-azobis-isobutyronitrile (AIBN) (Eastman Kodak, Co.) was recrystallized from methanol. The hydrophilic comonomer was acrylic acid (AAc) (Aldrich Co.) that was purified before use by vacuum distillation at 39° C./10 mmHg. The reaction solvent, dioxane, HPLC grade (Aldrich Co.) was used as received. The mixture of [meth-]acrylamide derivative, initiator, hydrophilic comonomer, and solvent formed the reaction mixture.

The molar feed ratio of NiPAAm to AAc was varied as 99:1, 98:2 and 97:3. The copolymerization was carried out in dioxane (80 wt %), with the amount of AIBN initiator of $1.219 \times 10^{-3}$ mols/L. The reaction proceeded at 60° C. for 18 hours. The resulting copolymer solution was diluted with fresh dioxane and added dropwise to a ten-fold excess of diethyl ether producing copolymer precipitation. The precipitated copolymer was isolated by filtration and drying. The isolated copolymer was redissolved in acetone and reprecipitated into ten-fold excess diethyl ether. The final, essential step of purification involved dialysis of aqueous copolymer solution through 12,000–14,000 molecular weight cut off (MWCO) dialysis membrane. Dialysis removed the residual unreacted monomer and all copolymer fractions with molecular weights smaller than the MWCO of the dialysis membrane, resulting in a purified copolymer product. The purified copolymer product was further freeze dried.

The removal of molecular weights below 12,000 from the synthesized copolymers was confirmed by gel permeation chromatography. The removal of unreacted monomers was confirmed by nuclear magnetic resonance.

The lower critical solution temperature (LCST) of the synthesized copolymers was evaluated by the cloud point determination method. In this method, 1 wt % solutions of synthesized copolymers in phosphate buffered saline were heated from 20 to 50° C. in 2-deg increments every 10 min. and the absorbance at 450 nm was measured. The cloud point, corresponding to the LCST was determined as the temperature at the inflection point in the absorbance versus temperature curve. NiPAAm homopolymer exhibited an LCST at 32° C. Copolymerization with hydrophilic comonomers shifted the LCST to the physiological temperature range of 36–38° C. NiPAAm/AAc copolymer containing 2 mol % of AAc exhibited the LCST at 37° C.

Figure 2:
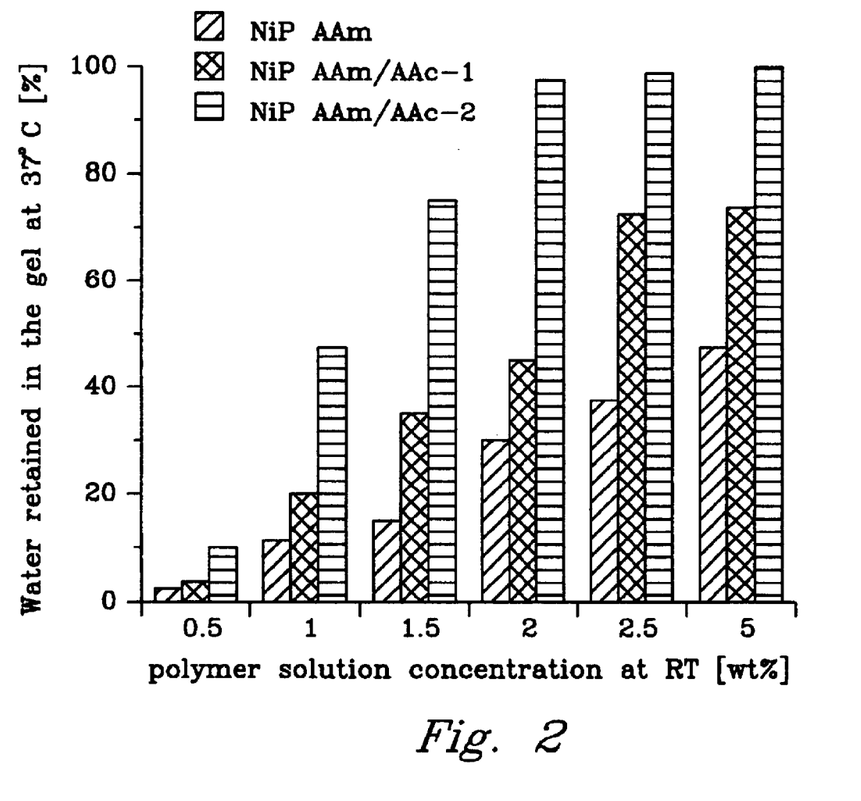
FIG. 2 is a bar graph of water retention in the gel versus initial copolymer concentration in the gelling solution.

Thermally reversible gel formation was studied at 37° C. The freeze dried copolymer was dissolved in phosphate buffered saline (PBS) at different copolymer concentrations (0.5, 1.0, 1.5, 2.0, 2.5, and 5.0 wt %) forming copolymer solutions. The PBS was specifically 0.15M NaCl, 0.01 M phosphates $KH_2PO_4$, and $Na_2HPO_4$. The copolymer solutions were thermally equilibrated at 37° C. for 24 hours. The syneresis (amount of water expelled from the gel) was measured gravimetrically. Syneresis of thermoreversible hydrogels of N-isopropylacrylamide (NiPAAm) and its copolymers with acrylic acid (AAc) was affected by copolymer composition (0, 1, 2 mol % of AAc) and polymer concentration as shown in FIG. 2. In FIG. 2 the amount of water retained in the gel is plotted as a function of the initial copolymer concentration in solution (before gelling). It was unexpectedly discovered that the solution containing at least about 2 wt % of the NiPAAm/AAc copolymer having at least about 2.0 mol % of AAc was able to produce a reversible gel exhibiting substantially no syneresis.

EXAMPLE 2

An experiment was conducted to confirm the necessity of the minimum gelling molecular weight cutoff. A gelling polymer solution was made as in Example 1, but the solution was not dialyzed so that no low molecular weight species were removed. The result was a solution, milky in appearance, that did not form a gel.

EXAMPLE 3

A further experiment was conducted to demonstrate the behavior of the gel during tissue perfusion in lymph nodes. A freeze dried copolymer of N-isopropylacrylamide with acrylic acid (2 mol %) NiPAAm/AAc)] was dissolved in PBS as in Example 1. A dye Naphthol blue-black, electrophoresis reagent, from Sigma was added to the copolymer solution. In all solutions, the dye was physically mixed by dissolving into the solutions, but was not covalently bonded to the copolymer.

Canine lymph nodes were freshly isolated and equilibrated at 37° C. PBS for 30 min.

Figure 3A:
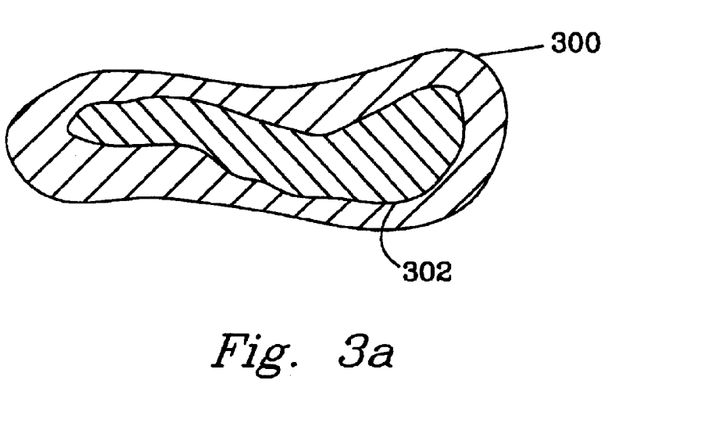
FIG. 3a depicts a lymph node sectioned after the injection of thermally reversible copolymer/dye solution.

A 5 wt % solution of NiPAAm/AAc in PBS, containing also a small amount (>0.01%) of the blue dye was prepared and cooled in an ice bath. Small aliquots (0.2–0.3 ml) of the cold polymer solution were injected into the freshly isolated canine lymph nodes. After the injection, lymph nodes were kept at 37° C. PBS for 10–15 min permitting the thermal gelation of the injected copolymer solution. The injected lymph nodes were then cut open with a razor blade to evaluate the extent of tissue perfusion. As shown in FIG. 3a, the dye perfusion within the lymph node 300 was limited to the extent of perfusion of the geled copolymer solution 302, and was clearly visible.

Figure 3B:
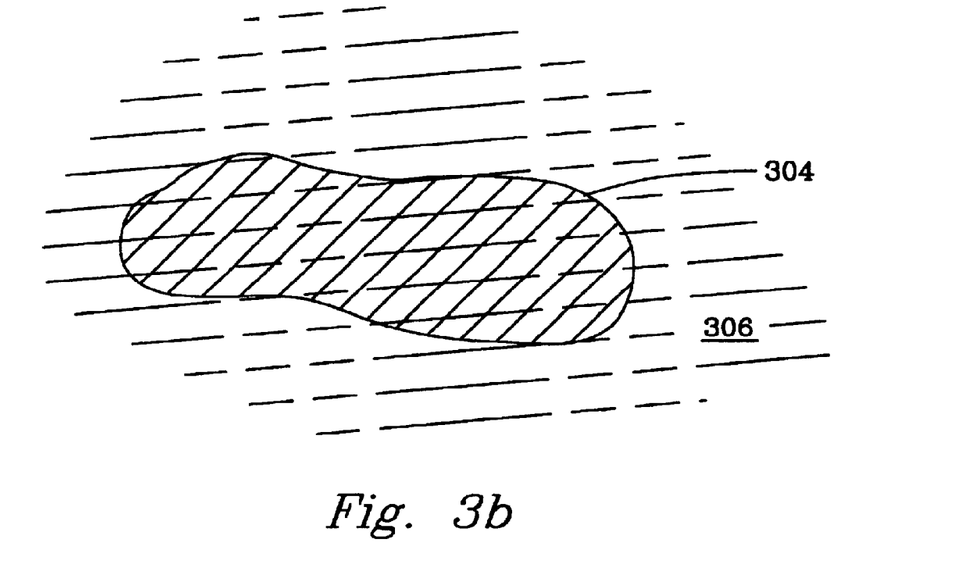
FIG. 3b depicts another lymph node sectioned after the injection of the dye solution alone.

As a control, dye solution in PBS only was injected into another lymph node 304 without mixing the dye into the gelling solution. Dye 306 was not contained locally within the lymph node but diffused throughout and beyond the lymph node as illustrated in FIG. 3b. Injection of the dye solution alone resulted in no dye localization within the lymph node 304.

EXAMPLE 4

An experiment was conducted to demonstrate containment of a radioisotope in a gel. A non-radioactive stable isotope proxy was used. Specifically, in vitro experiments were performed to evaluate the ability of the poly(NiPAAm-co-AAc) copolymer gel to entrap stable isotope forms of barium and yttrium salts within the gel matrix at 37° C.

The poly(NiPAAm-co-AAc) copolymer containing 2 mol % of acrylic acid was used for the experiments. This copolymer exhibited the gelling transition at 37° C. The following salts of barium and yttrium were tested: yttrium chloride, barium chloride and barium sulfate.

Yttrium Chloride ($YCl_3$)

Polymer solution (1) was prepared by dissolving 5.0 g of poly(NiPAAm-co-AAc) copolymer in 95.0 g of phosphate buffered saline (PBS). $YCl_3$ colloidal suspension was prepared by mixing 0.11 g of $YCl_3$ with 10 ml of PBS. An amount of 0.1 ml of the colloidal suspension was added to 0.9 ml of polymer solution (1) and mixed thoroughly. The mixed polymer solution was then placed in a test tube and incubated at 37° C. for 20 min. Formation of an opaque gel was observed. The amount of $YCl_3$ in the gel was 1100 µg.

After 20 min. of incubation, a 10 ml of PBS prewarmed to 37° C. was added to the test tube on the top of the gel. The gel layer stayed intact for the time of the experiment, and the added PBS did not mix with the gel layer.

The concentrations of $YCl_3$ in the PBS were tested after 33 min. and 24 hours by ICP/AES analysis. Detected concentrations were 0.12 µg/ml after 30 min. and 0.03 µg/ml after 24 hr. These correspond to 0.12% and 0.03% of total yttrium present in the gel. In conclusion, the poly(NiPAAm-co-AAc) copolymer gel localized $YCl_3$ very efficiently.

Barium Chloride ($BaCl_2$)

To prepare a $BaCl_3$ stock solution, 0.497 g of $BaCl_2$ was mixed with 5 ml PBS. Next, 0.1 ml of the stock solution was added to 0.9 ml of polymer solution (1) and mixed thoroughly. The mixed polymer solution mixture was then placed in a test tube and incubated at 37° C. for 20 min. Formation of an opaque gel was observed. The amount of $BaCl_2$ in the gel was 9036 µg.

After 20 min. of incubation, a 10 ml of PBS prewarmed to 37° C. was added to the test tube on the top of the gel. The gel layer stayed intact for the time of the experiment, and the added PBS did not mixed with the gel layer.

The concentrations of $BaCl_2$ in the PBS were tested after 33 min. and 24 hours by ICP/AES analysis. Detected concentrations were 30.95 µg/ml after 30 min. and 17.73 µg/ml after 24 hr. These correspond to 3.76% and 2.16% of the total barium present in the gel. In conclusion, the poly(NiPAAm-co-AAc) copolymer gel localized $BaCl_2$ less efficiently than $YCl_3$. The difference was due mainly to a higher water solubility of the $BaCl_2$ salt.

Barium Sulfate ($BaSO_4$)

$BaSO_4$ exhibits very low solubility in water. In order to prepare a $BaSO_4$/polymer suspension, 10.1 mg of $BaSO_4$ was added directly to 0.99 ml of polymer solution (1) and mixed thoroughly. The mixed polymer solution was then placed in a test tube and incubated at 37° C. for 20 min. Formation of an opaque gel was observed. The amount of $BaSO_4$ in the gel was 10,100 µg.

After 20 min. of incubation, a 10 ml of PBS prewarmed to 37° C. was added to the test tube on the top of the gel. The gel layer stayed intact for the time of the experiment, and the added PBS did not mixed with the gel layer.

The concentrations of $BaSO_4$ in the PBS were tested after 33 min. and 24 hours by ICP/AES analysis. Detected concentrations were 0.34 µg/ml after 30 min. and 0.28 µg/ml after 24 hr. These correspond to, respectively, 0.04% and 0.03% of the total barium present in the gel. In conclusion, the poly(NiPAAm-co-AAc) copolymer gel localized $BaSO_4$ equally efficiently as $YCl_3$.

EXAMPLE 5

An experiment was conducted to demonstrate the in vivo containment of a radioisotope carrier in a cancerous tumor. A preliminary study was conducted in mice to demonstrate administering therapeutic levels of polymer composite (gel) containing yttrium-90 to tumors growing in mice. The purpose of this study was to show that (1) Y-90 was contained within the polymer composite at the site of the injection, and that (2) cancer cells in the tumors were killed by the intense beta-particle radiation from the Y-90 in the polymer. It is well known that beta particle radiation is useful for treating cancer cells. However, the melanoma cell line is a radiation-resistant cancer requiring very high radiation doses for effective therapy. Very high radiation doses (greater than 1000 Gy, or 100,000 rads) would be needed for complete cell killing in melanoma. Therefore, the main objective of this study was to demonstrate the feasibility of safely delivering very high radiation absorbed doses to live mice. It is believed that this study was the first in which a radioisotope-polymer composite was administered as a therapeutic agent against solid tumors in live animals.

Materials and Methods

Animals

Twelve normal, six-to-eight-week old C57BL/6 female mice were obtained from Charles River Laboratories, were acclimatized on standard shredded pine-chip bedding in plastic laboratory cages, and were provided standard rodent chow and water ad libitum. All procedures and experiments were approved in advance by the Institutional Animal Care Committee.

Inoculations

Each of the 12 mice was inoculated with melanoma cells 12 days prior to the scheduled therapy injection. The cell line used was B16-F1 mouse melanoma from the 331 building stock. Approximately 50,000 viable tumor cells in 0.05 mL of cell culture medium (a concentration of about 1 million cells per mL) were administered subcutaneously into the inner anterior thigh/abdomen area.

Materials

Yttrium-90 chloride ($YCl_3$) was prepared as a solution in 0.05M HCl. Colloidal Y-90 was formed upon mixing with polymer solution in phosphate buffered saline. Approximately 2.6 mCi Y-90 were placed in each of six heavy shielded (beveled glass) vials (0.1 mL Kimax) stored in shielded aluminum overpack.

The polymer composite used was a thermally reversible copolymer gel composed of poly(N-isopropylacrylamide-co-acrylic acid) [NA2 polymer], as a 5 wt % solution in phosphate buffered saline (PBS). This thermally sensitive polymer is liquid at room temperature (22° C.). It solidifies at body temperature (37° C.). Approximately 0.1 mL of polymer was drawn by syringe and place into the Kimax vial containing the 2.5 mCi Y-90, and mixed prior to injection into a mouse tumor.

Approximately 0.1 mL Dexamethasone sodium phosphate U.S.P. (Dex), 3 mg/mL (Steris Laboratories, Inc., Phoenix) was administered to some of the tumors by needle injection. The purpose of the Dex was to reduce the intratumoral pressure. Fifteen minutes elapsed between injection of Dex and injection of Y-90 polymer composite.

Rubber-shielded syringes (0.5 to 1.0 cc) fitted with microfine needles (27 gauge) were used to administer the radioisotope composite solution to the mouse tumors.

Radioisotope Polymer Composite Injection

Ten mice were anesthetized, one at a time, with methoxyflurane (Pitman-Moore, N.J.). The mice were kept intermittently under an infra-red heating lamp to keep their body temperature at or above 37° C.

Each of these ten mice was injected with dexamethasone, NA2 polymer, or Y-90 solutions according to the treatment regimen summarized in Table E5-1.

Mice were sacrificed on day two after the therapy injection by $CO_2$ asphyxiation, and their tumor, liver, kidneys and spleen were excised and preserved for further examination and radiological counting for Y-90. The amount of Y-90 in the excised tissues (liver, kidney and spleen) was determined using a planar beta counter. The histopathology of the tumors was also examined.

TABLE E5-1

Injection regimes and survival

| Mouse number | Injection regime (total) Injection volume 100 µl | Comments |
|---|---|---|
| 1 | Dexamethasone + polymer + Y-90 | Alive on day 2, some skin burning observed on periphery of tumor |
| 2 | Dexamethasone + polymer + Y-90 | Alive on day 2 |
| 3 | Dexamethasone + polymer + Y-90 | Alive on day 2 |
| 4 | Polymer + Y-90 | Alive on day 2 |
| 5 | Polymer + Y-90 | Died on day 1, 2 large tumors |
| 6 | Polymer + Y-90 | Alive on day 2 |
| 7 | Dexamethasone + polymer | Died on day 2 |
| 8 | Dexamethasone + polymer | Died on day 1 |
| 9 | Polymer | Alive on day 2 |
| 10 | Polymer | Died on day 1 |

TABLE E5-1-continued

Injection regimes and survival

| Mouse number | Injection regime (total) Injection volume 100 µl | Comments |
|---|---|---|
| 11 | No treatment | Died on day 2 |
| 12 | No treatment | Died on day 2 |

TABLE E5-2

Weights of the excised tumors and organs on day 2 (necropsy)

| Mouse Number | Tumor [g] | Liver [g] | Kidney [g] | Spleen [g] |
|---|---|---|---|---|
| 1 | 3.4 | 0.8 | 0.32 | 0.03 |
| 2 | 1.6 | 0.64 | 0.40 | — |
| 3 | 3.5 | 0.7 | 0.25 | 0.04 |
| 4 | 1.78 | 0.89 | 0.32 | 0.05 |
| 6 | 1.23 | 0.74 | 0.38 | 0.08 |
| 7 | 1.2 | 0.98 | 0.32 | 0.07 |
| 9 | 2.4 | 0.60 | 0.28 | 0.07 |

TABLE E6-3

Isotope containment within the tumors

| Mouse number | Total Y-90 activity administered (microcuries) | Activity per sample on day 2 after injection (microcuries, decay-corrected to time of injection), and percent of administered activity | | | | | |
|---|---|---|---|---|---|---|---|
| | | Kidney | | Liver | | Spleen | |
| | | µCi | % | µCi | % | µCi | % |
| 1 | 2600 | 17.1 | 0.658 | 8.29 | 0.319 | 0.44 | 0.017 |
| 2 | 2600 | 40.0 | 1.538 | 16.9 | 0.650 | — | — |
| 3 | 2600 | 6.76 | 0.260 | 3.40 | 0.131 | 0.092 | 0.034 |
| 4 | 2600 | 18.8 | 0.723 | 19.4 | 0.746 | 0.71 | 0.027 |
| 5* | 2600 | — | — | — | — | — | — |
| 6 | 2600 | 9.91 | 0.381 | 3.33 | 0.128 | 0.11 | 0.004 |

*Mouse 5 died before necropsy

Pathology Report

Formalin fixed specimens from 7 mice were submitted in individual vials. The specimens were trimmed, inserted in plastic cassettes, and submitted to Our Lady of Lourdes Hospital in Pasco for the preparation of paraffin sections stained with hematoxylin and eosin.

The following information was provided: the mice had been injected subcutaneously with a melanoma cell line; the resulting tumors from 5 of the 7 mice (specimens labeled 1, 2, 3, 5, and 6) were injected with a soluble matrix of yttrium-90; the mice were killed 2 days after Y-90 injection; a high radiation dose from the Y-90 was delivered to the tumors; the specimens were stored for several weeks to allow for the decay of the Y-90; tumors from mice #1, 2, 3, and 7 were also injected with a corticosteroid; mice #7 and 9 were not injected with Y-90.

The purpose of the histopathologic examination was to determine whether the Y-90 had an effect on the tumors, and how that effect could be altered with corticosteroids.

Pathology Discussion

The tumors produced by the injected cell cultures resembled malignant melanomas. The necrosis observed was compatible with tumors of a high level of malignancy and also with the effect of high-dose irradiation and cell death. There were no clear difference in the necrosis between the Y-90 injected tumors and the tumors not injected with Y-90. It should be noted that the measurements provided were for only one sample from each specimen and are not intended to imply quantitative differences between the specimens.

The short (2-day) time period between therapy injection of Y-90 polymer composite and sacrifice would not have been sufficient for manifestation of extensive cell-killing. The tumors were well-advanced and necrotic, which made it difficult to isolate the radiotoxic effects of high-dose irradiation. In general, the mice treated with Y-90 appeared to be more healthy and active, even with large tumor burdens on day 2 after the injection, just before necropsy, than did the mice that were not treated with Y-90. The notable exception was mouse No. 5 with two large tumors. Mouse No. 5 died of causes apparently related to melanoma tumor burden on day 1.

Radiation Absorbed Dose Estimates

The Y-90 equilibrium dose constant is 1.99 g-rad/µCi-hr. The cumulated hours in the tumor for two days is 21.1 hrs (the integral of the time-activity curve for 100% retention in the tumor). Therefore, the radiation absorbed dose to a tumor of 3.5 g would be $$1.99 \times 2600 \times 21.1/3.5 = 31{,}200 \text{ rads } (312 \text{ Gy}).$$

For a 1.7 g tumor, the dose would be 64,200 rads (642 Gy).

Actual doses to tumors would be less than this amount, because some of the activity was excreted, and a fraction translocated to normal tissues. We do not have sufficient information on uptake and retention of Y-90 activity in normal organs for dose estimates.

Summary and Conclusions

This experiment showed the feasibility of administering a radioisotope polymer composite to solid tumors in animals. The experiment clearly demonstrated the ability of the gelling NA2 polymer to contain Y-90 radioisotope mostly at the injection site. The tumors remained very radioactive after administration, showing that most of the injected activity was retained at the injection site. Normal-tissue uptake was minimal (a few percent or less). Histopathology did not show a significant melanoma cell death from radiation because of the short time between injection and necropsy; however, the efficacy of treatment may have been obscured by the short time between injection and necropsy, and the advanced stage of the tumor development (extensive coagulative necrosis).

EXAMPLE 6

An experiment was conducted to demonstrate placement of Yttrium-90/technetium-99m-polymer composite into prostate tissue of two young, healthy beagle dogs.

Y-90/Tc-99m-polymer Composite

Yttrium-90 was prepared as a solution of $YCl_3$ in 0.05 N HCl. Colloidal Y-90 was formed upon mixing with polymer solution in phosphate buffered saline. The total amount administered to each dog prostate was approximately 1.1 mCi in a volume of 1.5 to 2.0 mL. Technetium-99m sulfur colloid (Mallincrodt Medical) (600 µCi, or 22 MBq, 100 µL by volume) was added to and mixed with the Y-90-polymer solution immediately prior to injection to facilitate in vivo gamma-camera imaging of the injected material.

Reversibly gelling copolymers of N-isopropylacrylamide and acrylic acid, poly(NiPAAm-co-acrylic acid), were tested as delivery vehicles for the Y-90 and Tc-99m radioisotopes. Two copolymers with different gelling temperatures were tested: NA-2 Sept. 97, with gelling temperature at 37° C. and NA-1.8 Feb. 2, 1998 that gels at 36° C.

Polymer solutions were prepared as follows: 5 wt % of poly(NiPAAm-co-acrylic acid) was dissolved in phosphate buffered saline. A 50 μL solution of $YCl_3$ (stable yttrium) suspension was added to obtain a diluted $YCl_3$ suspension with total stable yttrium concentration of 55 μg/mL. The suspension was steam-sterilized in an autoclave for 15 min. Directly before injection, an appropriate amount of this suspension was added to the vial containing the Y-90 radioisotope and mixed thoroughly.

Animals

Two beagle dogs were anesthetized for this study. Anesthesia given was injected Pentothal (15 mg/kg), with 0.625 Acepromazine and the same amount of Atropine plus Isoflurane gas and oxygen. The dogs' rectal temperatures were measured before and after the injections. The dogs were placed in a supine position on the operating table, and were immobilized. The hind legs were tied upward to facilitate the polymer injections. The ultrasound probe was placed in the rectum. The parallel grid template was affixed to the ultrasound probe.

Injection Procedure

The Y-90/Tc-99m-polymer composite was injected using two to four needles inserted through a parallel grid template.

Gamma Imaging

Portable gamma camera was used to image the localization of technetium-99m gamma rays from the polymer composite.

Dog 1 Procedure and Results

The initial rectal temperature was 38.0° C., and the final temperature was 36.3° C.

The surgeons had difficulty identifying/defining the position of the prostate due to a large pubic arch and small gland size (2.5 cm wide, 1.5 cm int.-post.), volume approx. 7 $cm^3$.

The amount and polymer batch injected was 1.6 mL of NA-2 September 1997, having a gelling temperature 37° C.

The Y-90/Tc-99m-polymer composite was maintained on ice before injection. Two needles were used, and four squirts of 0.2 mL (200 μL) were administered through each needle.

Gamma-camera imaging was performed immediately after the polymer composite was administered to the prostate gland. The images showed liver uptake (approx. 20% within 10 min. after the injection). A possible cause for early liver uptake may have been a direct injection into the vasculature and trauma to the prostate after multiple needle puncture. The polymer may not have had an opportunity to gel completely because the dog body temperature was slightly below the polymer gelation point (36.3 vs. 37° C.).

Dog 2 Procedure and Results

The initial rectal temperature was not measured. The final rectal temperature was 36.6° C. The prostate of Dog 2 was easier to locate. There was no pubic arch problem. The prostate gland was slightly larger, with an estimated volume of 10 $cm^3$ (4×3 cm).

The amount and polymer batch administered were 2.0 mL of NA-1.8 Feb. 2, 1998, having a gelling temperature 36° C. The Y-90-polymer composite was maintained at room temperature prior to injection into Dog 2. Four needles were used to administer the polymer composite. Injections consisted of 0.5 mL (500 μL) per needle as three squirts per needle of about 0.17 mL per squirt. Each squirt was given after withdrawing the needle approximately 1 cm.

Gamma-camera imaging was conducted immediately after the injections, acquiring approximately 200,000 counts. The images showed no specific liver uptake within 10 min. after the injection.

It appears that the polymer did gel completely in Dog 2 because the dog body temperature was slightly above the polymer gelation point (36.6 F. vs. 36° C.).

Post Injection Procedures for Dog 1 and 2

Animals were sacrificed on day 9 after the injection of the Y-90/Tc-99m-polymer composites. Samples of the prostate, liver, lung, heart, kidney, and spleen tissues were collected and the activity of Y-90 in the tissues was determined in pCi/gm per unit wet weight. The results are summarized in Table E7-1. As shown, after nine days in vivo, the concentrations of Y-90 in the prostate of Dog 2 were significantly higher than concentrations of Y-90 in other tissues of the animal. Tissue counts for Dog 1 demonstrate no specific localization of Y-90 in the prostate tissue. These results are consistent with gamma imaging results showing that the surgeions completely missed the target tissue (prostate) during their injection procedure. There was also significant liver uptake of Tc-99m in Dog 1 and no liver uptake in Dog 2. The results are also consistent with the fact that polymer used for Dog 1 had a higher gelling transition temperature (37° C.) and did not gel during the injection because Dog 1 body temperature was below 37° C. (36.3° C.). Therefore radioisotope localization did not occur in Dog 1. However, localization did occur in Dog 2.

TABLE E7-1

The Y-90 activities measured in tissue samples collected on day 9 post injection.

|  | Wet Weight (g) | Y-90 Activity (pCi/gm) |
|---|---|---|
| Dog 1 |  |  |
| Heart | 0.6475 | 11.4 |
| Kidney | 0.4712 | 211 |
| Liver | 0.6510 | 214 |
| Lung | 0.3587 | 342 |
| Spleen * | 0.0704 | 51.5 |
| Prostate | 1.2450 | 37.7 |
| Dog 2 |  |  |
| Heart | 2.1700 | 4.44 |
| Kidney | 0.7028 | 112 |
| Liver | 1.1765 | 104 |
| Lung | 1.6691 | 362 |
| Spleen | 0.6935 | 50.4 |
| Prostate | 1.7588 | 13650 |

Conclusions

The results of Y-90 counts and gamma imaging are consistent with the fact that gelling temperatures of the injected polymers were different and that polymer used for the Dog 1 procedure did not completely gel (the Dog 1 body temperature was slightly below the polymer gelation point: 36.3 vs. 37° C.). Hence, the results presented clearly illustrate the importance of gelling polymer in localization of the injected radioisotopes.

This experiment showed excellent localization of radioisotope polymer composite in the target tissue (prostate) of Dog 2 with minimal radionuclide activity in other non-target tissues at 9 days post injection subsequent autoradiography of Dog 2 prostate showed uniform distribution of the Y-90 polymer composite throughout the prostate gland.

Closure

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A radioisotope carrier, comprising:
   (a) a stimulus-sensitive methacrylamide gelling polymer in an aqueous solution which gelling polymer changes from a first fluent state to a second, less fluent state upon exposure to an increase in temperature, a change in ionic strength, and/or a change in pH, wherein the gelling polymer remains in the second, less fluent state upon dilution; and
   (b) an aqueous insoluble or confined radioisotope mixed with said gelling polymer as said radioisotope carrier.

2. A radioisotope carrier comprising:
   a gelling copolymer comprising
   (a) a linear random copolymer in an aqueous solvent, having
      (i) an [meth-]acrylamide derivative; and.
      (ii) a hydrophilic comonomer; said linear random copolymer in the form of a plurality of linear chains having a plurality of molecular weights greater than or equal to a minimum gelling molecular weight cutoff;
   (b) the aqueous solvent mixed with said linear random copolymer as a reversible gelling solution; and
   (c) an aqueous insoluble or confined radioisotope mixed with said gelling copolymer as said radioisotope carrier.

3. The radioisotope carrier as recited in claim 2, wherein an amount of said hydrophilic comonomer in the linear random copolymer is less than about 10 mole %.

4. The radioisotope carrier as recited in claim 3, wherein said amount is about 2 mole %.

5. The radioisotope carrier as recited in claim 2, wherein said [meth-]acrylamide derivative is an N,N'-alkyl substituted [meth-]acrylalmide.

6. The radioisotope carrier as recited in claim 5, wherein said N,N'-alkyl substituted [meth-]acrylamide is selected from the group consisting of N-isopropyl[meth-]acrylamide, N,N'-diethyl[meth-]acrylamide, N-[meth-]acryloylpyrrolidine, N-ethyl[meth-]acrylalmide, and combinations thereof.

7. The radioisotope carrier as recited in claim 2, wherein said hydrophilic comonomer is hydrophilic [meth]acryl-compound.

8. The radioisotope carrier as recited in claim 7, wherein said hydrophilic [meth-]acryl-compound is selected from the group consisting of [meth-]acrylamide, hydrophilic [meth-]acrylic acid ester, hydrophilic [meth-]acrylamide derivatives and combinations thereof.

9. The radioisotope carrier as recited in claim 8, wherein said hydrophilic [meth-]acrylamide derivatives are selected from the group consisting of N,N-diethyl[meth-]acrylamide, 2-[N,N-dimethylamino]ethyl[meth-]acrylamide, 2-[N,N-diethylamino]ethyl[meth-]acrylamide, or combinations thereof.

10. The radioisotope carrier as recited in claim 8, wherein said hydrophilic [meth-]acrylic ester is selected from the group consisting of 2-[N,N-diethylamino]ethyl[meth-]acrylate, 2-[N,N-dimethylamino]ethyl[meth-]acrylate, and combinations thereof.

11. The radioisotope as carrier as recited in claim 2, wherein said aqueous solvent is selected from the group consisting of water, and aqueous salt solution.

12. The radioisotope carrier as recited in claim 11, wherein said salt solution is a phosphate buffered saline.

13. The radioisotope carrier as recited in claim 12, wherein an amount of said solvent is from about 70 wt % to about 99 wt %.

14. The radioisotope carrier as recited in claim 1, wherein said radioisotope is selected from the group consisting of yttrium-90, indium-111, radium-223, actinium-225, bismuth-212, bismuth-213, scandium-47, astatine-211, rhenium-186, rhenium-188, iodine-131, iodine-124, lutetium-177, holinium-166, ~amarium-153, copper-64, copper-67, phosphorus-32 and combinations thereof.

15. The radioisotope carrier as recited in claim 1, wherein said confined radioisotope is selected from the group of chelators, capsules and combinations thereof.

16. The radioisotope carrier as recited in claim 15, wherein said chelators are selected from the group consisting of 1,4,7,10-tetraazacyclododecane-N,N',N",N"'-tetraacetic acid (DOTA), tetra-butyl-calix[4]arene-crown-6-dicarboxylic acid (TBBCDA), 5,11,17,23-tetra-t-butyl-25,26,27,28-tetrakis (carboxymethoxy)-calix[6]arene (HBHC), diethylenetriamine-pentaacetic acid (DTPA), EDTA, and combinations thereof.

17. The radioisotope carrier as recited in claim 15, wherein said capsules are selected from the group of glass beads, polymer beads and combinations thereof.

18. The radioisotope carrier as recited in claim 1, further comprising a contrast agent.

19. The radioisotope carrier as recited in claim 18, wherein said contrast agent is selected from the group of gamma-emitting radioisotope, ultrasound contrast enhancing agent, paramagnetic isotope, positron-emitting radioisotope and combinations thereof.

20. The radioisotope carrier as recited in claim 19, wherein said gamma-emitting radioisotope is selected from the group of Tc-99m, In-111, Rh-186, Rh-188, Th-201, Ga-67, Y-86, Y-91, I-131, F-18, Cu-64, Cu-67, As-74, Zr-89 and combinations thereof.

21. The radioisotope carrier as recited in claim 19, wherein said ultrasound contrast enhancing agent is a plurality of air-filled albumin-coated microspheres, human serum albumin with octofluoropropane.

22. The radioisotope carrier as recited in claim 19, wherein said paramagnetic isotope is gadolinium.

23. The radioisotope carrier as recited in claim 22, wherein said gadolinium is a chelate selected from the group consisting of gadolinium-DTPA, gadolinium-EDTA and combinations thereof.

24. A radioisotope carrier, comprising:
   (a) a reversible stimulus-sensitive methacrylamide gelling polymer in an aqueous solution which gelling polymer changes from a liquid state to a gel state upon exposure to a change in temperature, ionic strength, sheer stress, and/or in pH, wherein the gelling polymer is in a liquid state at temperatures in a range of from about 20° C. to about 30° C.; and
   (b) an aqueous insoluble or confined radioisotope mixed with said gelling polymer as said radioisotope carrier.

25. A radioisotope carrier, comprising:
   (a) a reversible stimulus-sensitive methacrylamide gelling polymer in an aqueous solution which gelling polymer changes from a first fluent state to a second, less fluent state upon exposure to a specific stimulus comprising a change in temperature, ionic strength, sheer stress, and/or pH, wherein the gelling polymer reverses from the second, less fluent state to the first fluent state only when the specific stimulus is reversed; and
   (b) an aqueous insoluble or confined radioisotope mixed with said gelling polymer as said radioisotope carrier.

* * * * *